(12) United States Patent
Jacofsky et al.

(10) Patent No.: US 9,277,829 B2
(45) Date of Patent: Mar. 8, 2016

(54) SYSTEMS AND METHODS FOR MONITORING AND PROVIDING THERAPEUTIC SUPPORT FOR A USER

(75) Inventors: Marc C. Jacofsky, Phoenix, AZ (US); David J. Jacofsky, Peoria, AZ (US)

(73) Assignee: TC13—Pressure Applications LLC, Phoenix, AZ (US)

( * ) Notice: Subject to any disclaimer, the term of this patent is extended or adjusted under 35 U.S.C. 154(b) by 0 days.

(21) Appl. No.: 13/188,721

(22) Filed: Jul. 22, 2011

(65) Prior Publication Data
US 2013/0019408 A1    Jan. 24, 2013

(51) Int. Cl.
*A47C 31/12*     (2006.01)
*A47C 27/08*     (2006.01)
*A61G 7/057*     (2006.01)
(Continued)

(52) U.S. Cl.
CPC ............. *A47C 31/123* (2013.01); *A47C 27/083* (2013.01); *A61B 5/447* (2013.01); *A61B 5/6832* (2013.01); *A61G 7/05776* (2013.01); *G06F 19/3406* (2013.01); *A61B 5/0022* (2013.01); *A61B 5/0024* (2013.01); *A61B 5/7275* (2013.01); *A61B 2562/028* (2013.01); *A61B 2562/0247* (2013.01); *A61G 2203/34* (2013.01); *A61G 2203/46* (2013.01); *A61G 2205/60* (2013.01)

(58) Field of Classification Search
CPC ........... A61G 7/05769; A61G 2203/34; A61G 7/05776; A61G 2203/46; A61G 2205/60; A61G 2203/03; A47C 27/082; A47C 27/10; A47C 27/083; A47C 31/123; A61B 5/447; A61B 5/6832; A61B 5/0022; A61B 2562/028; A61B 2562/0247; A61B 5/7275; A61B 5/0024; G06F 19/3406

USPC ................... 5/713, 615, 715, 710–712, 706; 177/144
See application file for complete search history.

(56) References Cited

U.S. PATENT DOCUMENTS 4,542,547 A * 9/1985 Sato ................................. 5/713
5,044,029 A    9/1991 Vrzalik
(Continued)

FOREIGN PATENT DOCUMENTS

JP    2010-286971 A    12/2010

OTHER PUBLICATIONS

European Search Report for EP 12817138.6, mailed May 4, 2015, 9 page.

*Primary Examiner* — Robert G Santos
*Assistant Examiner* — Myles Throop
(74) *Attorney, Agent, or Firm* — Sterne, Kessler, Goldstein & Fox P.L.L.C.

(57) ABSTRACT

A method for monitoring pressure at one or more points on an individual and automatically adjusting one or more sections of a support structure. The method includes periodically receiving pressure data from one or more radio frequency addressable sensors placed on an individual; determining, based on the received pressure data, whether an adjustment in the support structure is required; systematically adjusting cells located within the plurality of zones, one zone at a time, until an improvement in pressure data is indicated. If an improvement in pressure data is indicated for a zone, systematically adjusting cells within the plurality of subzones for that zone, one subzone at a time, until an improvement in pressure data is indicated. If an improvement in pressure data is indicated for a subzone, systematically adjusting cells in that subzone, one cell at a time, until an improvement in pressure data is indicated.

25 Claims, 16 Drawing Sheets

(51) Int. Cl.
*G06F 19/00* (2011.01)
*A61B 5/00* (2006.01)

(56) References Cited

U.S. PATENT DOCUMENTS

| | | | |
|---|---|---|---|
| 6,145,143 A | 11/2000 | Hicks et al. | |
| 6,216,300 B1 | 4/2001 | Hannagan | |
| 6,421,859 B1 | 7/2002 | Hicks et al. | |
| 6,463,336 B1* | 10/2002 | Mawhinney | 607/156 |
| 6,560,804 B2* | 5/2003 | Wise et al. | 5/713 |
| 6,591,437 B1 | 7/2003 | Phillips | |
| 6,874,185 B1 | 4/2005 | Phillips et al. | |
| 6,892,405 B1* | 5/2005 | Dimitriu et al. | 5/615 |
| 7,225,488 B2 | 6/2007 | Wu | |
| 7,444,704 B2* | 11/2008 | Phillips et al. | 5/713 |
| 7,583,199 B2 | 9/2009 | Graebe, Jr. | |
| 7,685,662 B2 | 3/2010 | Viard | |
| 7,784,131 B2 | 8/2010 | Genaro et al. | |
| 7,786,874 B2* | 8/2010 | Rodgers | 340/573.1 |
| 7,789,086 B2* | 9/2010 | Hyde et al. | 128/845 |
| 7,802,332 B2 | 9/2010 | Kummer et al. | |
| 7,849,544 B2 | 12/2010 | Flocard et al. | |
| 7,849,545 B2 | 12/2010 | Flocard et al. | |
| RE43,532 E * | 7/2012 | Menkedick et al. | 5/618 |
| 8,306,666 B2* | 11/2012 | Huber et al. | 700/275 |
| 2006/0065060 A1 | 3/2006 | Ito et al. | |
| 2006/0179579 A1 | 8/2006 | Phillips et al. | |
| 2007/0199154 A1 | 8/2007 | Escaross | |
| 2008/0091092 A1* | 4/2008 | Al-Ali | 600/310 |
| 2008/0201847 A1 | 8/2008 | Menkedick et al. | |
| 2009/0088608 A1* | 4/2009 | Mumford et al. | 600/300 |
| 2010/0109848 A1 | 5/2010 | Blair et al. | |
| 2010/0298742 A1* | 11/2010 | Perlman et al. | 600/595 |
| 2011/0004276 A1 | 1/2011 | Blair et al. | |
| 2012/0003933 A1* | 1/2012 | Baker et al. | 455/41.2 |
| 2012/0010525 A1* | 1/2012 | Jacofsky et al. | 600/561 |
| 2013/0006151 A1* | 1/2013 | Main et al. | 600/587 |
| 2013/0340176 A1* | 12/2013 | Stevens et al. | 5/710 |

* cited by examiner

SYSTEMS AND METHODS FOR MONITORING AND PROVIDING THERAPEUTIC SUPPORT FOR A USER

FIELD OF THE INVENTION

The present invention is related to systems and methods for monitoring pressure exerted on an individual at one or more points by a support structure and adjusting the support structure, in response to the monitored pressure.

BACKGROUND

The prevention and treatment of bedsores (and similar pressure injuries) is a serious issue facing hospitals and other healthcare facilities. Bedsores (also known as decubitus ulcers or pressure sores) result from prolonged pressure on an area. For example, a bedsore is a tissue injury that develops when soft tissue is compressed between a bony prominence and an external surface for a prolonged period of time. Bedsores are most likely to form on the back of the head, the sacrum, heels, ankles, buttocks, or shoulders. Bedsores are painful and can be life-threatening to patients, particularly the elderly and disabled. Excessive pressure on recent surgical incisions can lead to wound healing complications with similar etiology. The National Decubitus Foundation estimated that as many as 16% of the population of U.S. hospitals, alone, suffered from some form of pressure wound such as a bedsore.

Bedsores are most common for patients confined to a bed, chair or wheelchair. These furniture support systems often include padding made from cotton, feathers, foam, or the like. Some techniques for preventing bedsores focus on the design of the furniture and padding. To ease pressure, furniture has been introduced that include a fixed quantity of air or liquid in one or more chambers to provide therapeutic benefits, including minimizing the severity of pressure points on a user's body. In addition, some of these support systems include manual or programmable adjustable cushion sections. However, these systems cannot be adjusted based on feedback about the current condition of a patient and therefore, a patient may still develop bedsores using therapeutic furniture. Once a bedsore develops it is important to mitigate continued excessive pressure to the region to facilitate the healing process.

Another typical method for preventing bedsores involves frequent repositioning of a patient. However, this method of prevention is highly time consuming for medical and care facilities, particularly facilities having a large number of disabled or immobile patients. What is therefore needed is a system that can automatically adjust a support structure (or external padding for furniture) based on pressure monitored on one or more areas of a patient.

BRIEF DESCRIPTION OF THE FIGURES

The accompanying drawings, which are incorporated herein, form part of the specification and illustrate embodiments of systems and methods for monitoring and providing therapeutic support for a user. Together with the description, the drawings further serve to explain the principles of, and to enable a person skilled in the relevant art(s) to make and use the systems and methods described herein. In the drawings, like reference numbers indicate identical or functionally similar elements.

DETAILED DESCRIPTION

The following detailed description of systems and methods for monitoring and providing therapeutic support for a user refers to the accompanying drawings that illustrate exemplary embodiments. Unless otherwise noted, all embodiments and examples should be considered prophetic examples. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware, software, and/or firmware. Any actual hardware, software, and/or firmware described are not meant to be limiting.

Presented herein are embodiments of systems and methods for monitoring pressure on a patient and adjusting a support structure accordingly. In one embodiment, a pressure monitor can continuously (or semi-continuously) measure contact pressures between a portion of a user's body and a section of a support surface of a support system, such as a hospital bed. For example, the pressure monitor can measure contact pressure between a support surface and the user's head, arms, legs, feet, arms, torso, or any other suitable location on the user.

In embodiments, a pressure monitor can be configured to transmit measured pressure data to a networkable device (e.g., a laptop computer, PDA, cell phone, a processor located in the bed, or other patient monitor) using RF communications. The networkable device can then send a signal to actuators located within the bed to adjust the pressure of one or more sections in the support surface of the bed. The networkable device can additionally communicate the user's status and condition to a healthcare provider station (e.g., staffed by nurses, doctors, and other hospital personnel) or directly to a healthcare providers' wireless networkable device (e.g. cell phone, pager, or personal digital assistant (PDA)) through a communication network such as a local area network (LAN), wide area network (WAN), or the like. This communication allows the healthcare provider to remotely monitor a user, such as a hospital patient and take action when certain conditions are indicated. The networkable device, or associated computing system, can additionally record and display temporal trends, minima, and maxima in the pressure data and optionally log the data to the patient's electronic health records. The networkable device, or associated computing system, can also compare the pressure data to the patient's diastolic blood pressure or other measurement, and calculate relevant clinical gradients in real time.

Figure 1B:
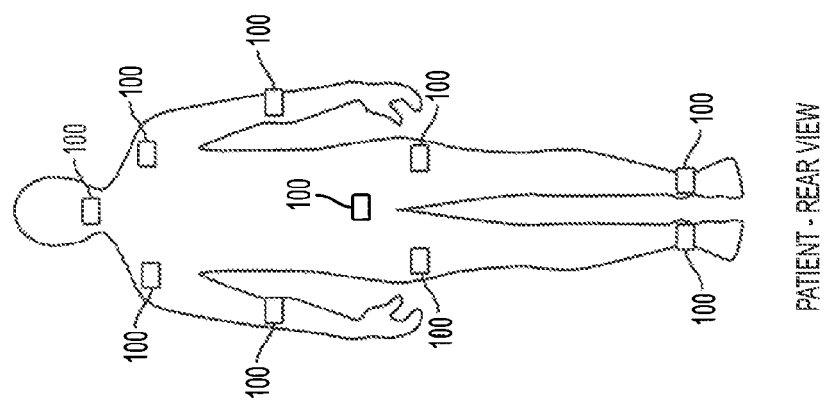
FIGS. 1A and B illustrate an exemplary operating environment for a system for monitoring pressure for an individual confined for a period of time to a support structure, such as a bed or a chair, according to embodiments of the present invention.
Figure 1A:
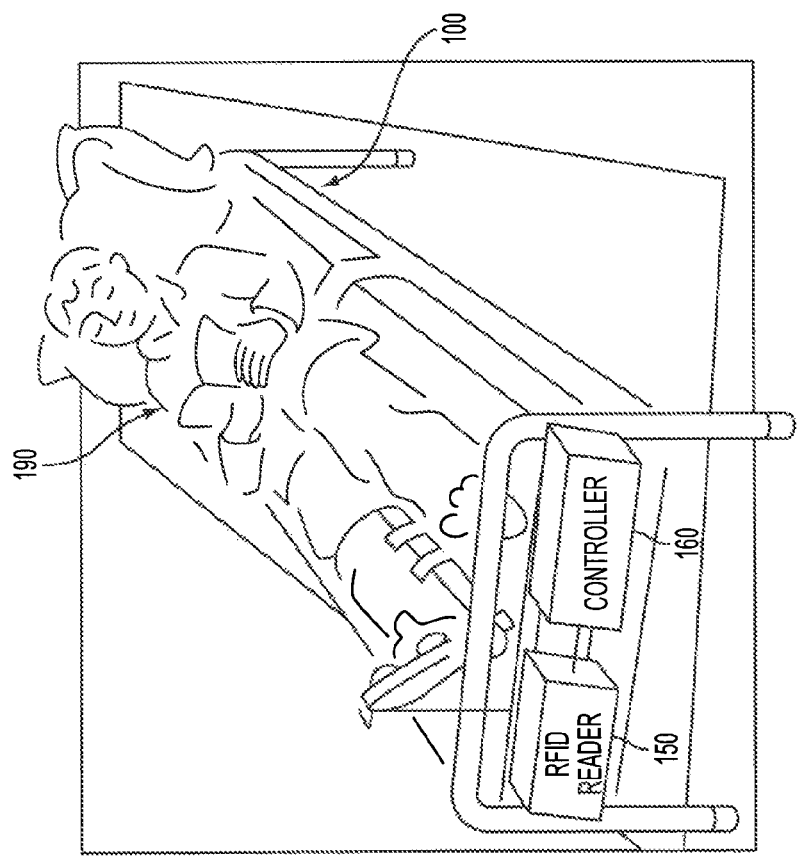

FIGS. 1A and B illustrate an exemplary operating environment for a system for monitoring pressure for an individual confined to a support structure for a period of time, such as a bed or a chair, according to an embodiment of the present invention. As shown in FIG. 1A, the system includes a support system 110. In the example of FIG. 1A, the support system is depicted as a bed. However, as discussed in detail below, the support system may be a mattress pad, a chair such as wheelchair or a similar form of support. An individual, e.g., patient 190, comes into direct or indirect contact with the support system. As shown in FIG. 1A, the individual is lying on structure 110. However, in other embodiments, the individual may be sitting or reclining in a different position.

Prior to placement on the support structure, one or more RF addressable pressure sensors 100 are placed on the individual. These pressure sensors may be placed at locations highly susceptible to pressure injuries such as the sacrum, back of the head, elbows, shoulders, ankles, etc. In an embodiment, these sensors are placed on the skin of the patient in a location most likely to have direct or indirect contact with the support structure or upon which the support structure is likely to exert pressure. FIG. 1B is the rear view of a patient depicting exemplary placement of a plurality of RF addressable pressure sensors, according to embodiments of the present invention. RF addressable pressure sensors 100 are described in further detail below.

The system further includes an RFID reader 150 and a controller 160. Although depicted as separate components, RFID reader 150 and controller 160 could be implemented in a single structure. RFID reader 150 is configured to communicate with the one or more RF addressable pressure sensors 100 and obtain data therefrom. RFID reader 150 is placed proximate to the individual. Although FIG. 1A depicts the reader 150 attached to the foot of the bed, the RFID reader may be placed at any location to permit detection and access to the RF addressable sensors. For example, RFID reader 150 may be placed on the support structure, under the support structure, above the support structure, or next to the support structure (e.g., on a mobile station).

RFID reader 150 is coupled to a controller 160. In an embodiment, controller 160 is configured to receive data from reader 150 and to determine whether adjustments should be made to support structure to reduce pressure in one or more areas. In an alternative embodiment, reader 150 includes the logic to determine whether adjustments should be made to support structure. Controller 160 is further configured to cause adjustments to be made to the support structure.

In addition, RFID reader 150 and/or controller 160 may be connected to an external monitoring station. The communication infrastructure is described in further detail below.

Support Systems

Figure 2:
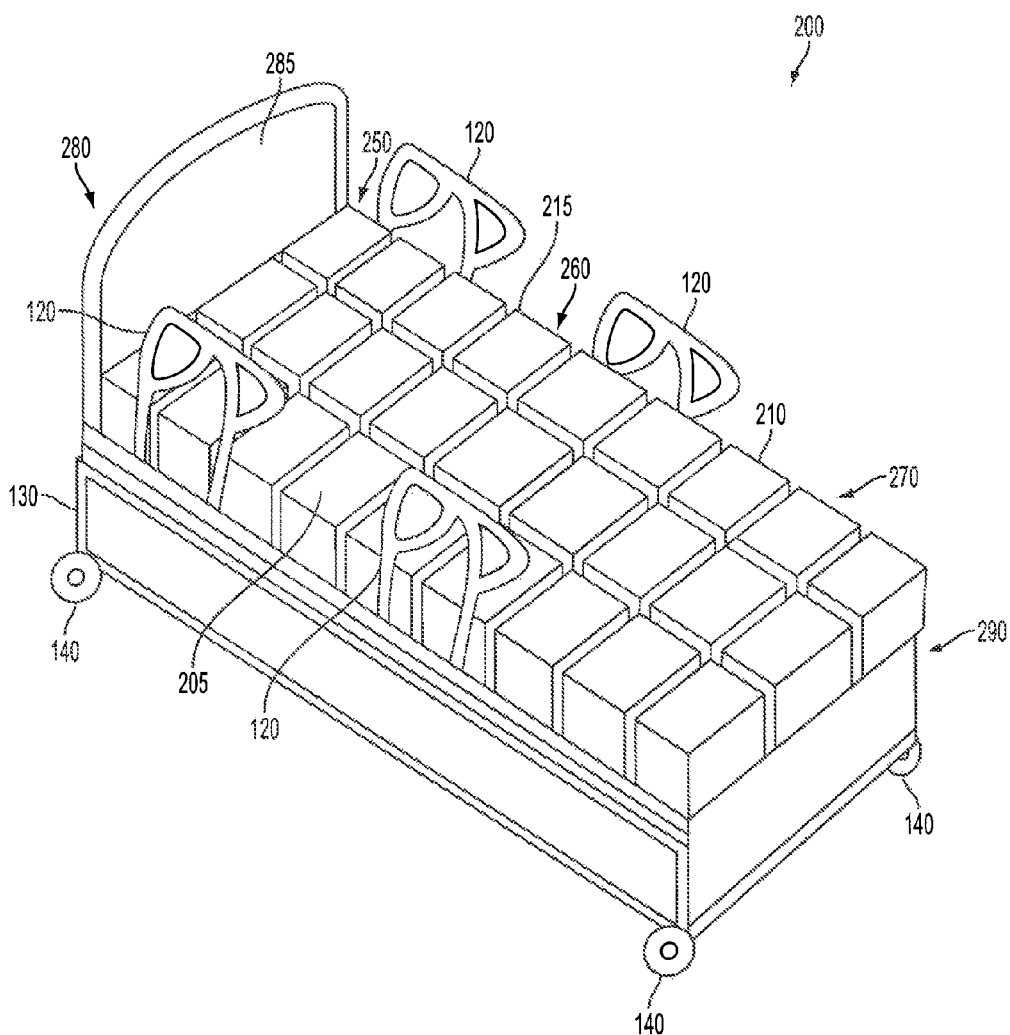
FIG. 2 is a perspective view of a support system incorporating a system for monitoring and providing therapeutic support for a user, in accordance with an embodiment of the present invention.

FIG. 2 is a perspective view of a support system 200 incorporating a system for monitoring and providing therapeutic support for a user, in accordance with an embodiment of the present invention. Support system 200 can be one of many forms, including but not limited to, a bed including a mattress and bed frame, such as a hospital bed configured for use during or after medical procedures, a conventional bed used for sleeping, a mattress for a bed, a mattress cover configured to be placed on top of a mattress, a chair such as a wheelchair, couch, or any other suitable support system having a support surface.

In some embodiments, support system 200 comprises conventional components of a hospital bed, for example mattress 215, head end 280 on one side of the mattress, including headboard 285, foot end 290 on the opposite side of mattress 215, bed frame 130 disposed underneath and supporting mattress 215, and side rails 120 for constraining a user within support system 200. Support system 200 can further include wheels 140 to facilitate moving the system. Alternatively, the support system can be in the form of a padded layer to be placed on top of a mattress, chair, couch, or other surface.

In some embodiments, mattress 215 can include a support surface 205 which includes areas corresponding to a conventionally sized user's body. For example, head portion 250 can be configured to receive the user's head, torso portion 260 can be configured to receive the user's torso, and leg portion 270 can be configured to receive the user's legs and feet. Mattress 215 can further include a plurality of adjustable sections 210. In some embodiments, each of adjustable sections 210 are in the shape of a square and are arranged to form a square grid, in other embodiments, one or more of adjustable sections 210 can be in the form of a shape other than a square. For example, a non-square rectangle, an oval, a sphere, a cylinder, or any other suitable geometric shape. In some embodiments, one or more sections can be shaped to contour the shape of the user's body. For example, mattress 215 can include a single adjustable section or a plurality of adjacent adjustable sections formed to provide a recess contour for the user's head.

In some embodiments, adjustable sections 210 of mattress 215 include a confined gas, liquid or other suitable flowable material. The support characteristics, such as inflation level can be adjusted with the aid of an air or liquid supply means, such as one or more pumps or a centralized facility air supply. In some embodiments, a single pump provides air to each of the sections. In other embodiments, multiple pumps provide air to multiple sections.

Figure 3:
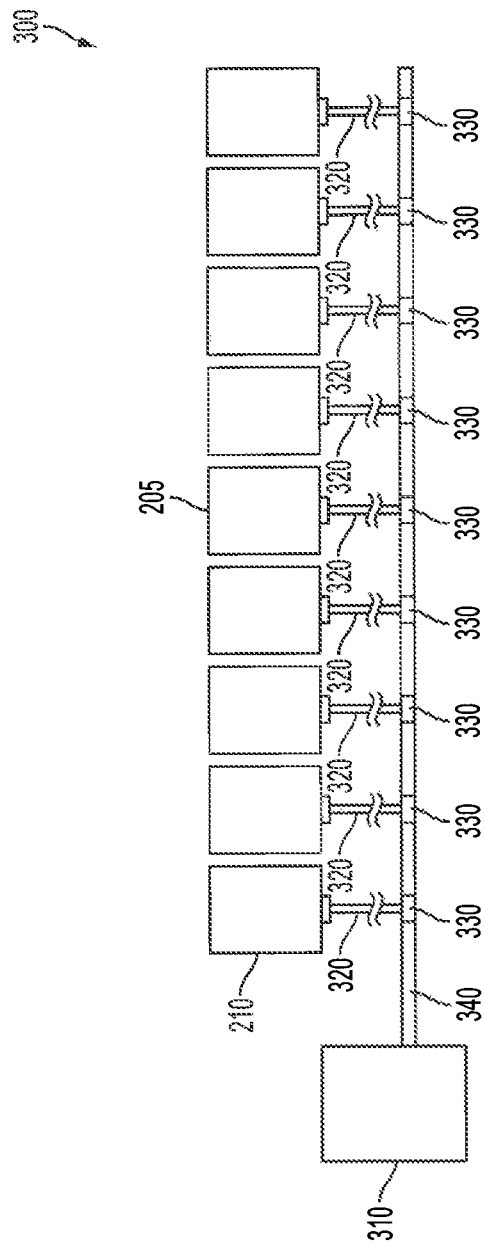
FIG. 3 is a schematic view of an air hose assembly of the support system of FIG. 2 in accordance with an embodiment of the present invention.

FIG. 3 is a schematic view of air hose assembly 300 of the support system of FIG. 2. In some embodiments, adjustable sections 210 are operatively connected to air pump assembly 310 to allow for inflation and deflation of adjustable sections 210. For example, air hose assembly 300 can be attached to central air line 340, which is then delivered through branch air lines 320 via line connections 330. Branch air lines 320 are also operatively connected to adjustable sections 210 to provide for inflation and deflation. Line connections 330 may include individual solenoid valves or other means of controlling flow into or out of each chamber.

Figure 4:
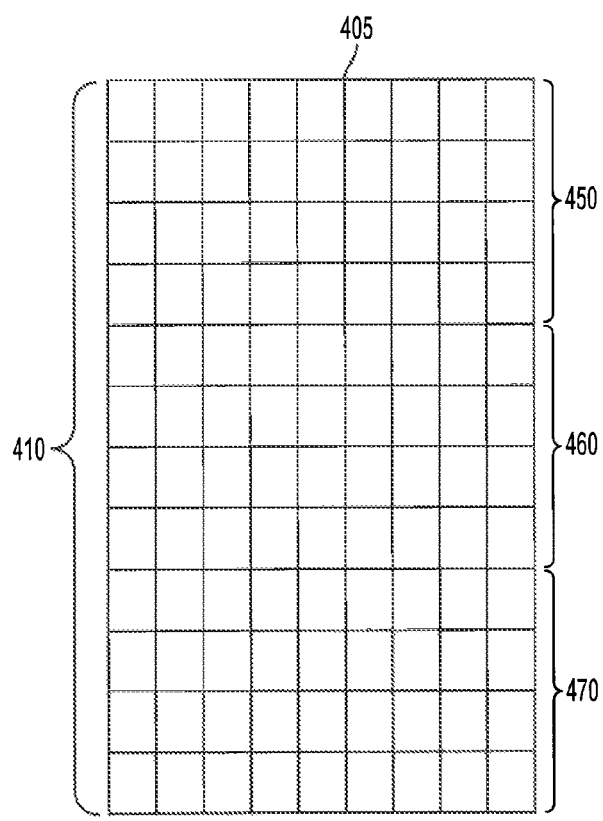
FIG. 4 is a schematic view of a support surface in accordance with an embodiment of the present invention.

FIG. 4 is a schematic view of a support surface 405 in accordance with an embodiment. Like support surface 205 of FIG. 2, support surface 405 comprises portions corresponding to a conventionally sized user's body. For example, head portion 450 can be configured to receive the user's head, torso portion 460 can be configured to receive the user's torso, and leg portion 470 can be configured to receive the user's legs and feet. Adjustable sections 410 can be smaller in size compared to adjustable sections 210 of support surface 205 shown in FIG. 2. Adjustable sections 210 can be of any suitable size and shape.

Figure 5:
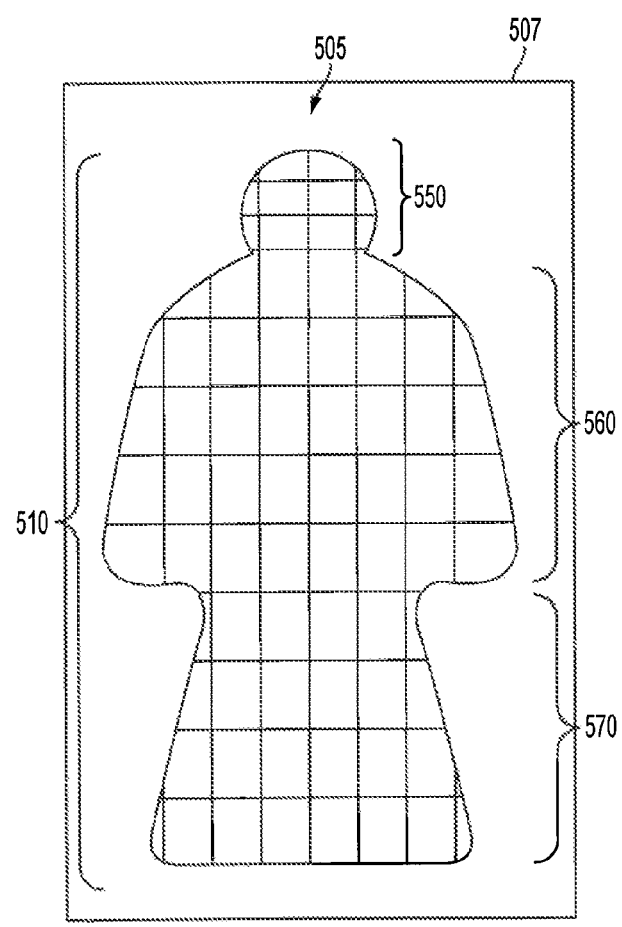
FIG. 5 is a schematic view of a support surface in accordance with an embodiment of the present invention.

FIG. 5 is a schematic view of a support surface 505 in accordance with an embodiment. Like support surface 205 of FIG. 2, support surface 505 comprises portions corresponding to a conventionally sized user's body. For example, head portion 550 can be configured to receive the user's head, torso portion 560 can be configured to receive the user's torso, and leg portion 570 can be configured to receive the user's legs and feet. Adjustable sections 510 can be arranged to generally follow the outline of the user's body in various conventional positions, as shown for Example in FIG. 2. In some embodiments, support surface 505 can further comprise an outer section 507 that surrounds the adjustable sections. Outer section 507 can comprise conventional bedding materials, such as foam or other padding, can alternatively comprise additional adjustable sections, non-adjustable inflated sections, or any suitable combination thereof.

Figure 6:
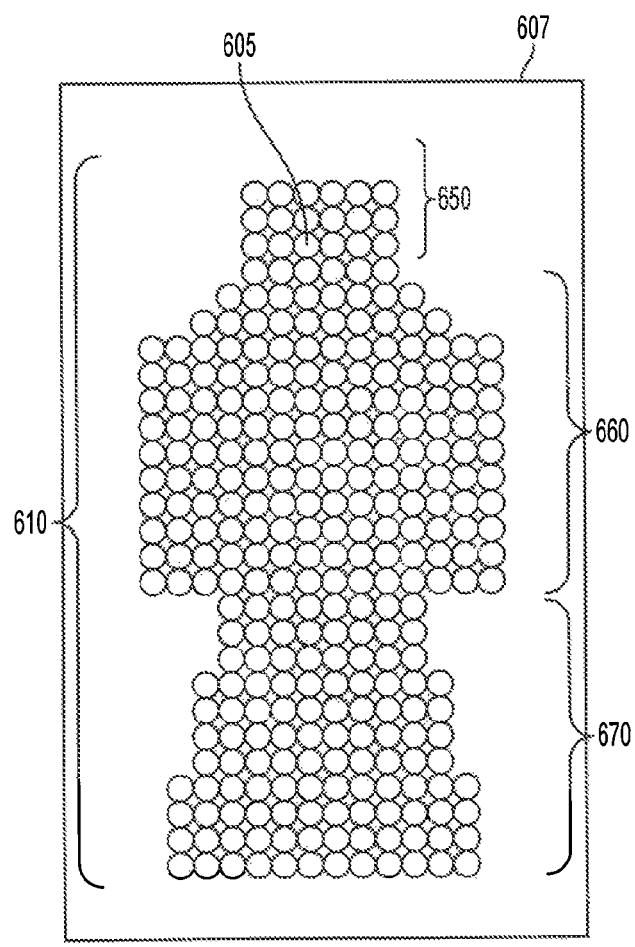
FIG. 6 is a schematic view of a support surface in accordance with an embodiment of the present invention.

FIG. 6 is a schematic view of a support surface 605 in accordance with an embodiment. Like support surface 205 of FIG. 2, support surface 605 comprises portions corresponding to a conventionally sized user's body. For example, head portion 650 can be configured to receive the user's head, torso portion 660 can be configured to receive the user's torso, and leg portion 670 can be configured to receive the user's leg and feet. Adjustable sections 610 can be arranged to generally follow the outline of the user's body in various conventional positions, as shown, for example, in FIG. 2. In some embodiments, support surface 605 can further comprise an outer section 607 that surrounds the adjustable sections. Outer section 607 can comprise conventional bedding materials, such as foam or other padding, can alternatively comprise additional adjustable sections, non-adjustable inflated sections, or any suitable combination thereof. Adjustable sections 610 can be rectangular in shape and smaller in size compared to adjustable sections 210 shown in FIG. 2 and adjustable sections 410 shown in FIG. 4. Adjustable sections 610 can be of any suitable size and shape.

RF Addressable Pressure Monitor

Figure 7:
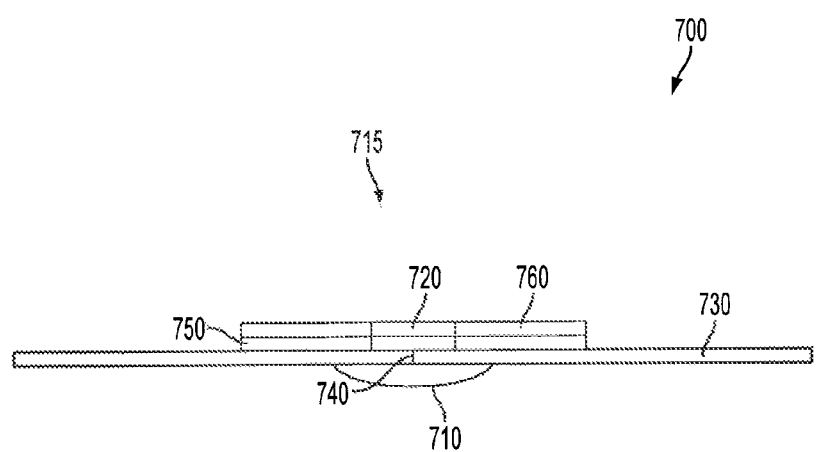
FIG. 7 is a schematic view of a pressure monitor in accordance with an embodiment of the present invention.

FIG. 7 is a schematic view of an RF addressable pressure monitor 700 in accordance with an embodiment presented herein. In some embodiments, RF addressable pressure monitor 700 is configured to be placed on a user and comprises a pressure sensor 710 operatively connected to an RFID device 715 disposed on a substrate 730. In some embodiments, pressure sensor 710 is a microelectromechanical system (MEMS) sensor on the order of 1 mm. The relatively small size of a MEMS pressure sensor allows easy placement on the user. Such MEMS sensors use a change in resistance, change in capacitance, change in voltage, or a piezoelectric effect to convert changes in pressure on a sensing membrane to a voltage, current, or frequency change in the output signal.

Pressure sensor 710 is coupled to a wire 740 coupled to a radiofrequency (RF) device 715 on substrate 730, which can be in the form of a surface patch or bandage. Substrate 730 can include an adhesive material on one surface for affixing to the skin of the patient. Substrate 730 can further include multiple layers. In some embodiments, RF device 715 and RF antenna 760 can be integrated within layers of substrate 730.

In some embodiments, pressure sensor 710 could be an air or fluid filled contained volume coupled to an appropriate sensor through a tube communicating with the sensing membrane. The sensor could therefore be separate from the bandage packaging.

In some embodiments, RF device 715 comprises a RF antenna 760 and a battery 750 coupled to RFID chip 720 to provide power and to transmit data. RF device 715 powers pressure sensor 710, and interprets or relays the data from pressure sensor 710 to an interrogating reader. The RF device can be passive, pass-active (battery assisted), or fully active (battery dependent) depending upon the frequency of desired reads, the estimated distance of the interrogating device from the RF device, and the power consumption needs of the RF device. In alternative embodiments, the pressure sensor is integrated with Bluetooth, ZIGBEE or other radios compatible with wireless devices such as cell phones.

Substrate 730 (e.g., a layer of an adhesive bandage) is used to maintain RF device 715 and battery 750 on the surface of the user's skin or clothing. In some embodiments, sterile gauze can be placed between the electronic components and the surface of the skin.

In operation, a pressure change between pressure sensor 710 and the support surface is registered at pressure sensor 710. In the embodiment shown, the pressure data is then communicated to RF device 715 coupled to pressure sensor 710. In the embodiment shown, pressure sensor 710 and RF device 715 are powered by battery 750. Battery 750 can be substantially rigid or can be flexible. As would be appreciated by persons of skill in the art, RF device 715 and/or pressure sensor 710 can be powered by other techniques. Adhesive bandage material can be used to house and maintain RF device 715, battery 750, and pressure sensor 710. Additional external sensors can further be included in pressure monitor 700, e.g., in the adhesive bandage material or on substrate 730. Sterile gauze can be present in between adhesive bandage or substrate 730 and the surface of the user's skin or clothing.

Figure 8:
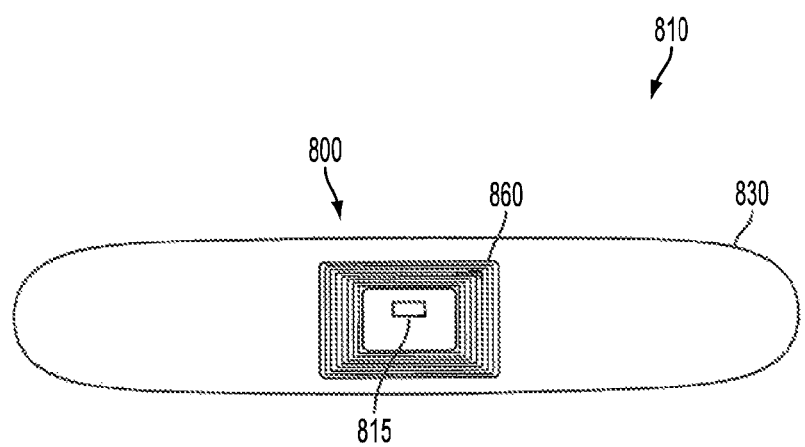
FIG. 8 is a top view of a bandage incorporating a pressure monitor in accordance with an embodiment of the present invention.

FIG. 8 is a top view of a bandage 810 incorporating a pressure monitor 800 and substrate 830 in accordance with an embodiment presented herein. Similar to the pressure monitor shown, for example, in FIG. 7, pressure monitor 800 can comprise an RF device 815 and RF antenna 860. In the embodiment illustrated in FIG. 8, the RF device is placed on top of substrate 830. In FIG. 8 the bandage is an oval shape, of course the bandage could be any other suitable shape. Bandage 810 can be used with any of the pressure monitors described above.

Figure 9:
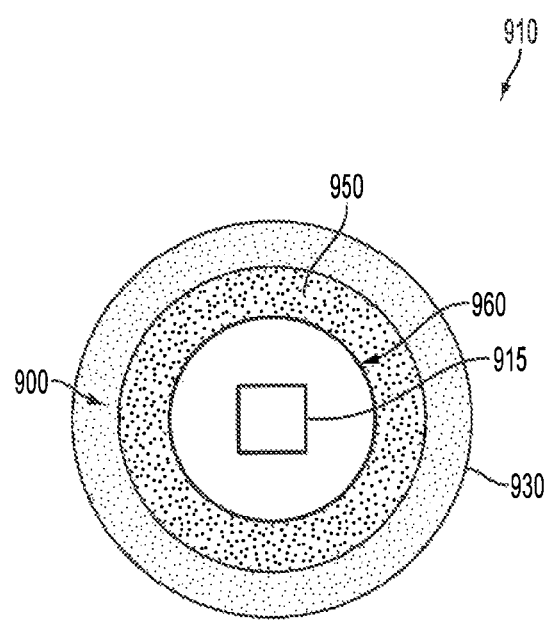
FIG. 9 is a top view of an alternate embodiment of a bandage incorporating a monitor in accordance with an embodiment of the present invention.

FIG. 9 is a top view of a bandage 910 incorporating a pressure monitor 900 and substrate 930 in accordance with an embodiment presented herein. Similar to the pressure monitor shown, for example, in FIG. 7, pressure monitor 900 can comprise an RF device 915, RF antenna 960, and battery 950.

Figure 10:
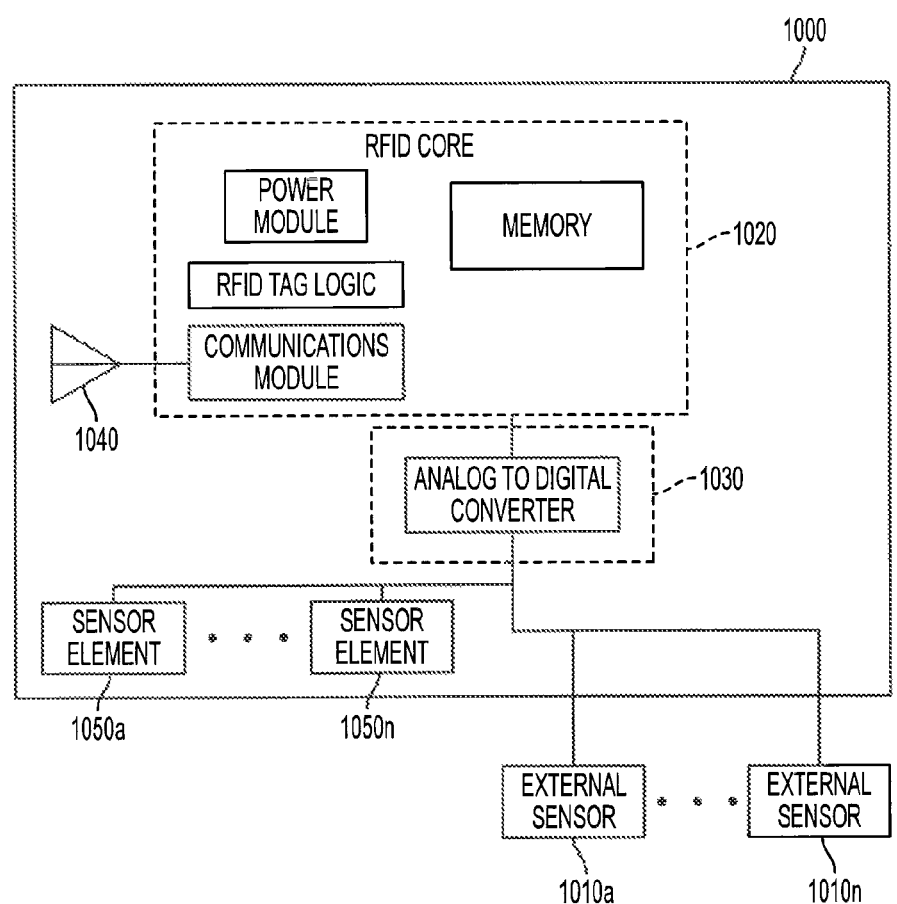
FIG. 10 is an RF device in accordance with an embodiment of the present invention.

FIG. 10 is an RF device 1000 according to an embodiment. RF device 1000 is coupled to one or more external sensors 1010a-1010n. RF device 1000 includes RF core 1020, an analog to digital converter (ADC) 1030, and one or more antennas 1040. These components are mounted or formed on a substrate. Additionally, the RF core 1020 and/or ADC 1030 can be included in an integrated circuit. RF device 1000 can also include one or more sensor elements 1050a-1050n. Sensor elements 1050a-1050n can be included in the integrated circuit, on the substrate, external to substrate, or in any combination of the above. Any compatible sensor element can be used as sensor element.

External sensors 1010a-1010n include the sensors (e.g., MEMS sensor) described above for measuring compartment pressure. These external pressure sensors can be coupled to a pressure probe through a wire connector or an inelastic fluid filled tube. In an alternate embodiment, a fiber optic connection can be used.

Various types of sensor elements can be implemented as sensors 1050a-1050n or external sensors 1010a-1010n. For example, integrated or external sensor can include a temperature sensor element that generate information indicating ambient temperature; a pH sensor element; or other biological or chemical sensors. The system can include other types of sensor elements or combinations thereof, as would be apparent to persons skilled in the relevant art(s). Testing has shown that some RFID reader chips are not well suited to read complex RFID sensors due to timing and/or power issues. The readers are essentially meant to read ID numbers and have a very short interrogation/response cycle time. Furthermore when the technology is passive (as is the case for most RFID) substantial power fluctuations occur on the RFID chip and this affects sensor accuracy.

RFID core 1020 includes a communications module coupled to antenna 1040, an RFID tag logic module, a power module and memory. In an embodiment, the memory stores an identifier for the RFID tag associated with the pressure sensor. The tag identifier, for example, may be used to associate the RF addressable sensor with an individual. In this example, a provider could maintain a database mapping tag identifiers to individuals.

A modified RFID chip can be used to facilitate these readers to read the pressure monitors comprising a complex MEMS sensor. Such a modified chip includes a serial peripheral interface (SPI) port and allows pre-processed sensor data to be stored in memory directly linked to the ID interrogation process of the RFID tag. This type of RFID tag therefore serves as a low cost "pass-through" radio. This design and method allows any sensor to be connected to common RFID technology and be read directly with current RFID enabled cell phones. The technology can be configured for ISO 15693 tags for example and is directly compatible with multiprotocol 13.56 MHz RFID reader chips for cell phones such as the PN 544 C2 reader chip made by NXP.

Figure 11:
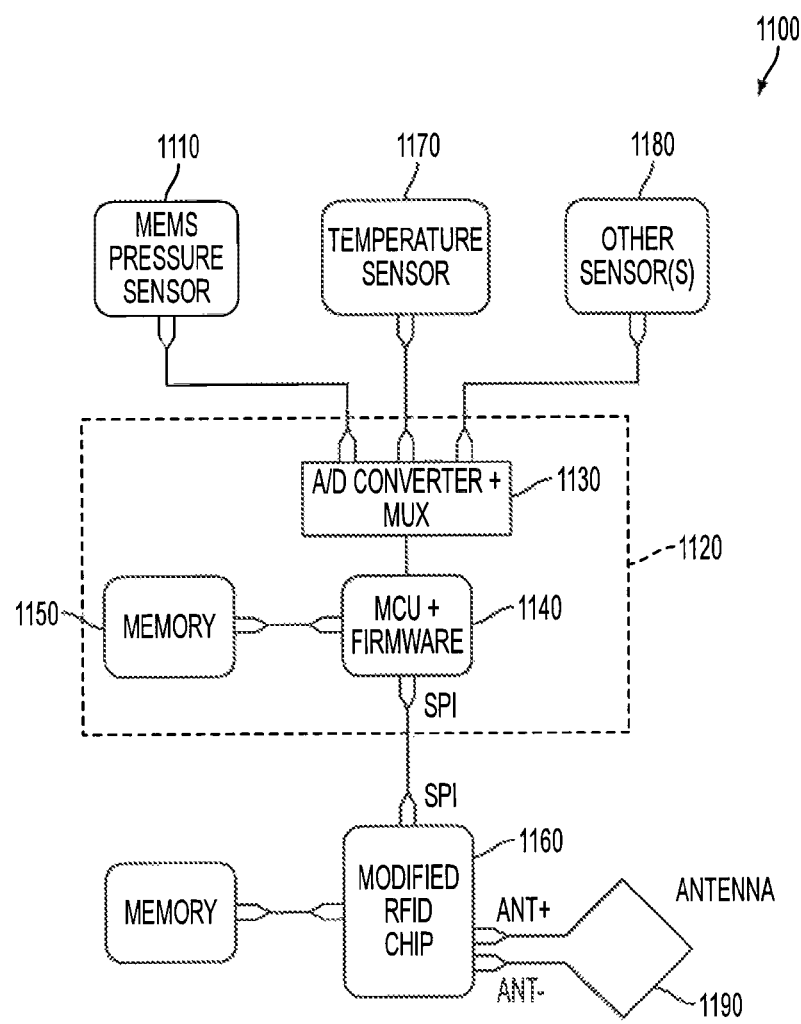
FIG. 11 depicts an exemplary system having a modified RFID chip, in accordance with an embodiment.

Different circuit designs and options are possible for the pass through method. FIG. 11 depicts an exemplary system 1100 having a modified RFID chip, and antenna 1190 according to an embodiment. FIG. 11 illustrates how complex sensors can be handled using a passive modified RFID radio, where the processed sensor data is passed through the RFID core as part of the standard interrogation-transmission of RFID data. The system 1100 includes a plurality of external sensors. In embodiments, the plurality of external sensors includes a complex calibrated external MEMS sensor 1110 and an ultra-precise external thermistor to allow medical grade combined pressure and temperature sensor measurements.

Each of the plurality of external sensors is coupled to a sensor interface 1120. Sensor interface 1120 includes an analog to digital converter (ADC) and multiplexer 1130, an external microprocessor (MCU) and firmware 1140, and memory 1150. Using an external microprocessor and firmware allows compression of complex sensor data and extremely fast passage of information via the RFID chip, well within the limits of current standard RFID reader chips. Sensor interface 1120 further includes an external power source (e.g. battery, energy harvesting, solar, chemical, motion, etc.) that also can include a reference voltage calibration circuit. In an embodiment, sensor interface 1120 is included in a separate chip.

Sensor interface 1120 is coupled to modified RFID chip 1160. The command set for the external MCU 1140 is passed through the RFID chip 1160. The memory on the RFID chip is cleared either when full or bumped with each new interrogation or sensor data download or by external command from the RFID interrogator (e.g., a cell phone, or other wireless networkable device).

The RFID chip 1160 and sensor interface 1120 of FIG. 11 can be integrated into a single hybrid chip, whereby the packaged sensor data is placed in memory and where the main processor would be powered by the external power source and the communication part built to handle the constraints imposed by current RFID interrogators. Alternatively, the components of sensor interface 1120 can be included in a separate integrated circuit chip.

Various designs are possible for the fully integrated chip. The system of FIG. 11 illustrates the combination of an external temperature sensor 1170, external MEMS sensor 1110, and other sensor(s) 1180. For temperature on chip a single calibration point digital sensor can be used. Such sensor technology is described in U.S. Pat. No. 7,461,972 that is included by reference in its entirety.

Network

Figure 12:
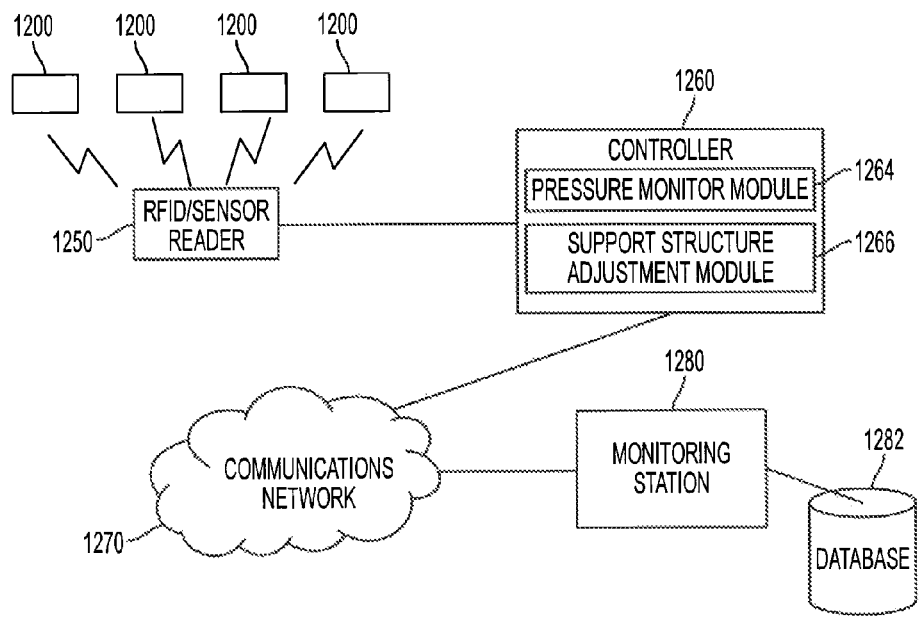
FIG. 12 is a block diagram of an illustrative network for remotely monitoring one or more sensors integrated with RF devices, in accordance with an embodiment of the present invention.

FIG. 12 is a block diagram of an illustrative network for monitoring one or more pressure sensors integrated with RF devices and adjusting a support structure to accommodate for changes in pressure, in accordance with an embodiment of the present invention. The network includes one or more RF addressable sensors 1200, one or more RFID/sensor readers 1250 and a controller 1260. Exemplary RF addressable sensors are described above. The network may optionally include a communications network 1270 coupled to the controller 1260 and a remote monitoring station 1280.

Communications network 1270 is a publicly accessible communications network. Communications network 1270 may be a wired network, wireless network, or a combination therefore. In another embodiment, communications network 1270 is a private network or a hybrid network including public and private portions. Persons skilled in the relevant art(s) will recognize that various network architectures could be used for communication network 1270.

Wireless RFID/sensor reader 1250 includes logic to read sensor data and RFID tag data transmitted by RF addressable sensor 1200. In an embodiment, wireless RFID/sensor reader 1250 also includes logic to process the received sensor data. Wireless RFID/sensor reader 1250 can be any wireless device capable of communicating via an air interface protocol with RF addressable sensor 1200. In some embodiments, wireless RFID/sensor reader 1250 could be a wireless phone, a personal digital assistant (PDA), a computer having wireless communications capabilities, or other type of mobile, handheld, and/or computing device (e.g., an iPAD).

According to an embodiment, signals are exchanged between the wireless RFID/sensor reader 1250 and RF addressable sensor 1200 according to one or more protocols. In an embodiment, reader 1250 and the RF addressable sensor 1200 communicate via a single protocol for both RFID tag communications and sensor communications. In an alternate embodiment, reader 1250 and RF addressable sensor 1200 communicate via a first protocol for RFID tag communications and via a second protocol for sensor communications. Examples of protocols used for RFID tag communications include binary tree traversal, HF ISO 15693 and EPC global Gen 2. An embodiment is also applicable to any other types of communication protocols between tags and readers otherwise known or yet to be developed.

RFID/sensor reader 1250 is coupled to a controller 1260. RFID/sensor reader 1250 communicates data obtained from the one or more RF addressable sensors 1200 to controller 1260. Controller 1260 includes a pressure monitoring module 1264 and a support structure adjustment module 1266.

Pressure monitoring module 1264 is configured to determine whether a pressure adjustment needs to be made to the support structure and isolates one or more cells to adjust. In an alternative embodiment, pressure monitoring module 1264 may be included as a component of RFID/sensor reader 1250 or distributed between the RFID/sensor reader and the controller 1260. Pressure monitoring module 1264 communicates adjustment information to support structure adjustment module 1266.

Support structure adjustment module 1266 is configured to adjust one or more cells in the support structure. In an embodiment, support structure adjustment module 1266 includes logic to determine the amount of adjustment to make to a specific cell. In an alternate embodiment, pressure monitoring module 1264 determines the amount of adjustment to make to a specific cell.

In an embodiment, controller 1260 and/or RFID/sensor reader 1264 communicates data to an external monitoring station. Controller 1260 and/or RFID/sensor reader 1250 may communicate all data obtained to external monitoring station 1280. In addition or alternatively, controller 1260 and/or RFID/sensor reader 1250 may communicate only when certain conditions are detected. For example, controller 1260 and/or RFID/sensor reader 1250 may alert the external monitoring station 1280 when pressure in a certain area remains elevated and/or is not reduced after a series of adjustments.

External monitoring station 1280 receives sensor data over network 1270, and processes the data. In an embodiment, the system associates tag identification data for an RF addressable sensor with an individual. External monitoring station 1280 may store data for each RF addressable sensors associated with an individual. The external monitoring station 1280 may analyze the pressure data associated with the individual and make an independent assessment of whether adjustments should be made to the support structure. External monitoring station 1280 may further be configured to communicate a request to adjust the structure to reduce pressure measurements for one or more tags associated with an individual. Records for individuals may be stored in a database 1282 coupled to external monitoring station 1280.

In an embodiment, a healthcare provider determines if medical intervention is necessary based on alerts from RFID/sensor reader 1264, controller 1266, and/or external monitoring station 1280. External monitoring station 1280 can display historical data or trends for one or more individuals.

Methods

Figure 13:
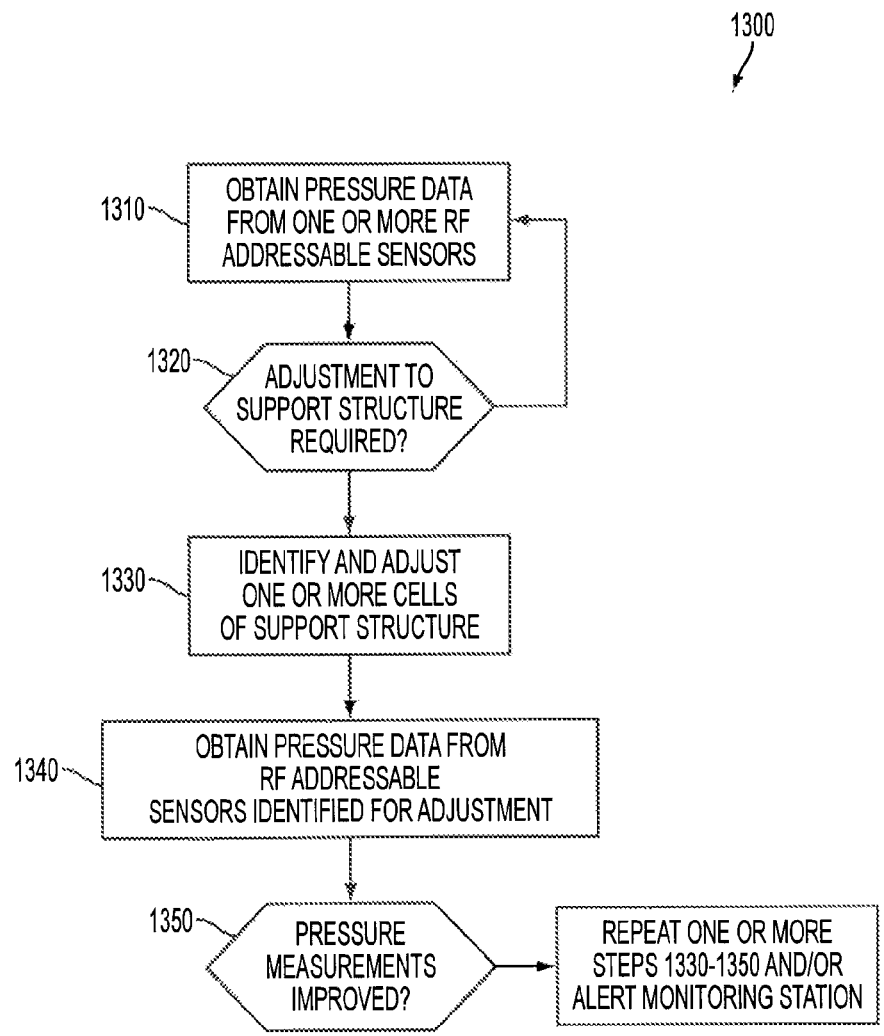
FIG. 13 is a flowchart illustrating a method of monitoring pressure, in accordance with an embodiment.

FIG. 13 is a flowchart 1300 of a method for monitoring pressure and adjusting a support structure to compensate for measured pressure, according to embodiments of the present invention. Flowchart 1300 is described with reference to the embodiment of FIG. 12. However, flowchart 1300 is not limited to that embodiment.

In step 1310, pressure monitoring module 1264 obtains pressure data from one or more RF addressable sensors 1200 placed on an individual. The pressure monitoring module 1264 may also obtain a tag identification number associated with the RF addressable sensor 1200 providing sensor data. In an embodiment, RFID/sensor reader 1250 polls the one or more RF addressable sensors 1200. In an alternate embodiment, the one or more RF addressable sensors 1200 are configured to periodically send data to RFID/sensor reader 1250. RFID/sensor reader 1250 then communicates the received data to pressure monitoring module 1264. In embodiments RFID/sensor reader 1250 may process the sensor data, e.g., to calibrate or smooth the received data, prior to communicating the data to pressure monitoring module 1264.

In step 1320, a determination is made whether the pressure data indicates an adjustment is required. In an embodiment, this determination is made on a per RF addressable sensor basis. For example, pressure monitoring module 1364 may determine for an RF addressable sensor whether the pressure data exceeds a threshold. In addition, or alternatively, the determination may be based on a historical trend for the RF addressable sensor. For example, if the pressure data has been consistently increasing over a predetermined period of time, an adjustment may be indicated for the RF addressable sensor. The networkable device, or associated computing system, can also compare the pressure data to the patient's diastolic blood pressure or other measurement, and calculate relevant clinical gradients in real time. As would be appreciated by persons of skill in the art, other techniques for determining whether an adjustment is required may be used with the present invention. If an adjustment is required, operation proceeds to step 1330. If no adjustment is required, operation returns to step 1310.

In step 1330, one or more cells of the support structure to be adjusted are identified and adjusted. One method for identifying the cell or cells to adjust is discussed in FIG. 14. As would be appreciated by persons of skill in the art, other techniques may be used in the present invention, e.g. triangulation of the sensors position by multiple RFID interrogators.

In step 1340, pressure monitoring module 1264 obtains pressure data from the RF addressable sensors identified for adjustment. In an embodiment, pressure data may be obtained from all RF addressable sensors, as in step 1310.

In step 1350, a determination is made whether the pressure measurements in the RF addressable sensors identified for adjustment has improved. If pressure measurements indicate that the pressure data still indicates adjustment is necessary, pressure monitoring module may repeat step 1340 and 1350 over a pre-defined period of time after an initial adjustment is made. If improvement is not realized over that period of time, pressure monitoring module 1264 may repeat step 1330 to alter the adjustments. Additionally, if no improvement is achieved, the pressure monitoring module 1264 may alert external monitoring station 1280 of a potential bedsore/pressure sore risk.

If pressure measurements indicate an improvement, the adjustments made in step 1330 may be maintained for a specific period of time. After that time has expired, the system may return the cell or cells to their status prior to the adjustment.

Figure 14:
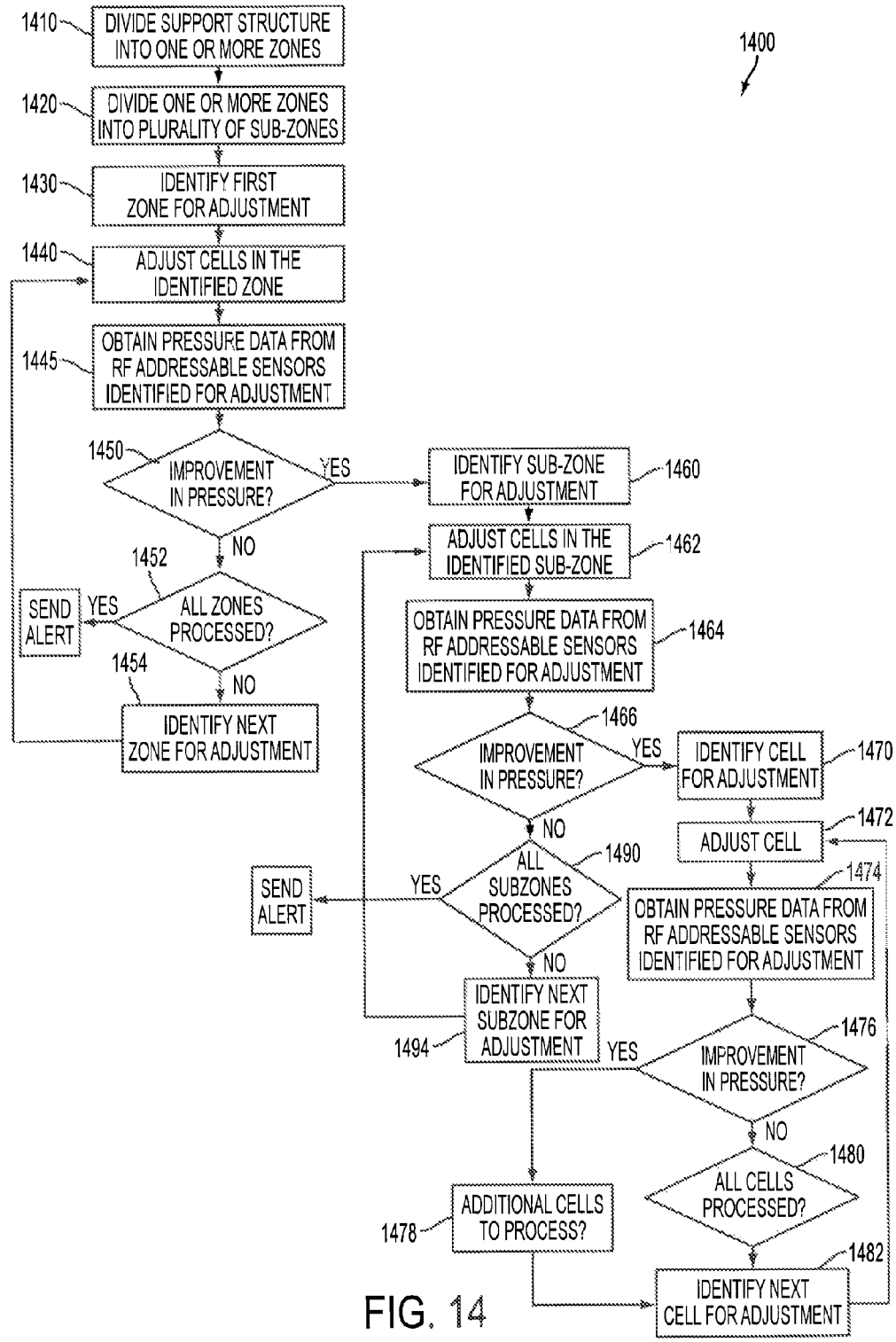
FIG. 14 is a flowchart showing a method for linking identifiers to create transparent and secure wireless monitoring of a user, in accordance with an embodiment.

FIG. 14 illustrates a flowchart 1400 for a method for determining an adjustment for one or more cells in a support structure, in accordance with embodiments of the present invention. FIG. 14 is described with reference to the embodiments of FIG. 12. However, the method is not limited to that embodiment.

Figure 15A:
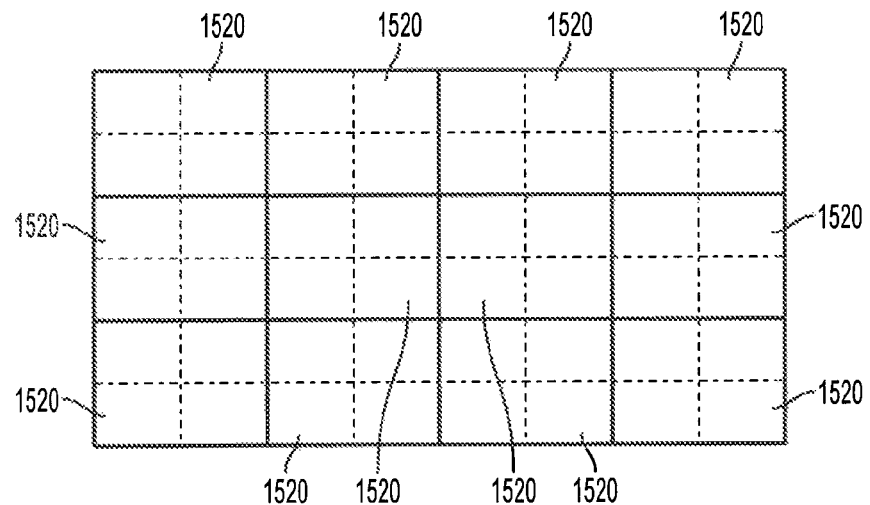
FIG. 15A depicts an exemplary support structure.
Figure 15B:
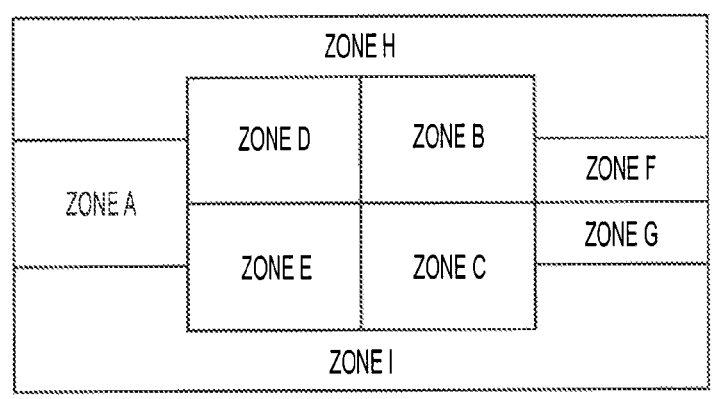
FIG. 15B depicts an exemplary support structure.

In step 1410, the support structure is divided into one or more zones or clusters. FIG. 15A depicts an exemplary support structure. As shown in FIG. 15A, the support structure is divided into a plurality of zones 1520. The zones may be of equal size and shape as shown in FIG. 15A. Alternatively, the zones may be defined based on the likely position of an individual on the support structure, as depicted in FIG. 15B. As would be appreciated by persons of skill in the art, other arrangements for zones could be used with the present invention.

In step 1420, one or more zones may be further divided into a plurality of sub-zones. FIG. 15A depicts a zone 1520 having a plurality of sub-zones. In embodiments, a sub-zone may be furthered divided into clusters. Step 1420 is optional.

In step 1430, a first zone for adjustment is identified. In an embodiment, the pressure monitoring module 1264 prioritizes zones based on likelihood of a pressure injury occurring in the zone. For example, the zone associated with an individual's sacrum may be prioritized first.

In step 1440, cells in the identified zone are adjusted. For example, the cells may be adjusted as described above in FIG. 3.

In step 1445, pressure data is obtained from RF addressable sensors identified for adjustment.

In step 1450, a determination is made whether an improvement in pressure is reflected in the obtained data. If an improvement is indicated, operation proceeds to step 1460. If no improvement is indicated by the data, operation proceeds to step 1452.

Note that steps 1440 and 1450 may be repeated over a pre-determined period of time before an action is taken to give time for pressure changes to be reflected.

In step 1452, a determination is made whether all zones in the support structure have been processed. If all zones have been processed, an alert may be sent to external monitoring station 1280 and processing of flowchart 1400 ends. If additional zones remain to be processed, operation proceeds to step 1454.

In step 1454, the next zone is identified. In embodiments, pressure monitoring module 1264 includes data specifying an order to process zones.

Operation then returns to step 1440.

In step 1460 (if improvement is indicated in step 1450), a sub-zone within the zone is identified. As with the zone, the pressure monitoring module 1264 may include data specifying an order to process sub-zones within a zone. Step 1460 is optional.

In step 1462, cells in the sub-zone are adjusted. For example, the cells may be adjusted as described above in FIG. 3.

In step 1464, pressure data is obtained from RF addressable sensor identified for adjustment.

In step 1466, a determination is made whether an improvement in pressure is reflected in the obtained data. If an improvement is indicated, operation proceeds to step 1470. If no improvement is indicated by the data, operation proceeds to step 1490.

Note that steps 1464 and 1466 may be repeated over a pre-determined period of time before an action is taken to give time for pressure changes to be reflected.

In step 1470, a first cell within the sub-zone (or zone) is identified. As with the zone, the pressure monitoring module 1264 may include data specifying an order to process cells within a zone or sub-zone.

In step 1472, the cell is adjusted. For example, the cell may be adjusted as described in FIG. 3.

In step 1474, pressure data is obtained from the RF addressable sensor identified for adjustment.

In step 1476, a determination is made whether an improvement in pressure is reflected in the obtained data. If an improvement is indicated, operation proceeds to step 1478. If no improvement is indicated by the data, operation proceeds to step 1480.

Note that steps 1474 and 1476 may be repeated over a pre-determined period of time before an action is taken to give time for pressure changes to be reflected.

In step 1478, a determination is made whether additional cells should be processed. If additional cells should be processed, operation proceeds to step 1480. If no additional cells are to be processed, operation ends.

In step 1480, a determination is made whether all cells in zone or sub-zone have been processed. If all cells have been processed, an alert may be sent to external monitoring station 1280 and processing of flowchart 1400 ends. If additional cells remain to be processed, operation proceeds to step 1482.

In step 1482, the next cell for adjustment is determined and operation returns to step 1472.

In step 1490, a determination is made whether all sub-zones in the support structure have been processed. If all sub-zones have been processed, an alert may be sent to external monitoring station 1280 and processing of flowchart 1400 ends. If additional sub-zones remain to be processed, operation proceeds to step 1494.

In step 1494, the next sub-zone is identified. In embodiments, pressure monitoring module 1264 includes data specifying an order to process zones.

Operation then returns to step 1462.

Computer Architecture

Figure 16:
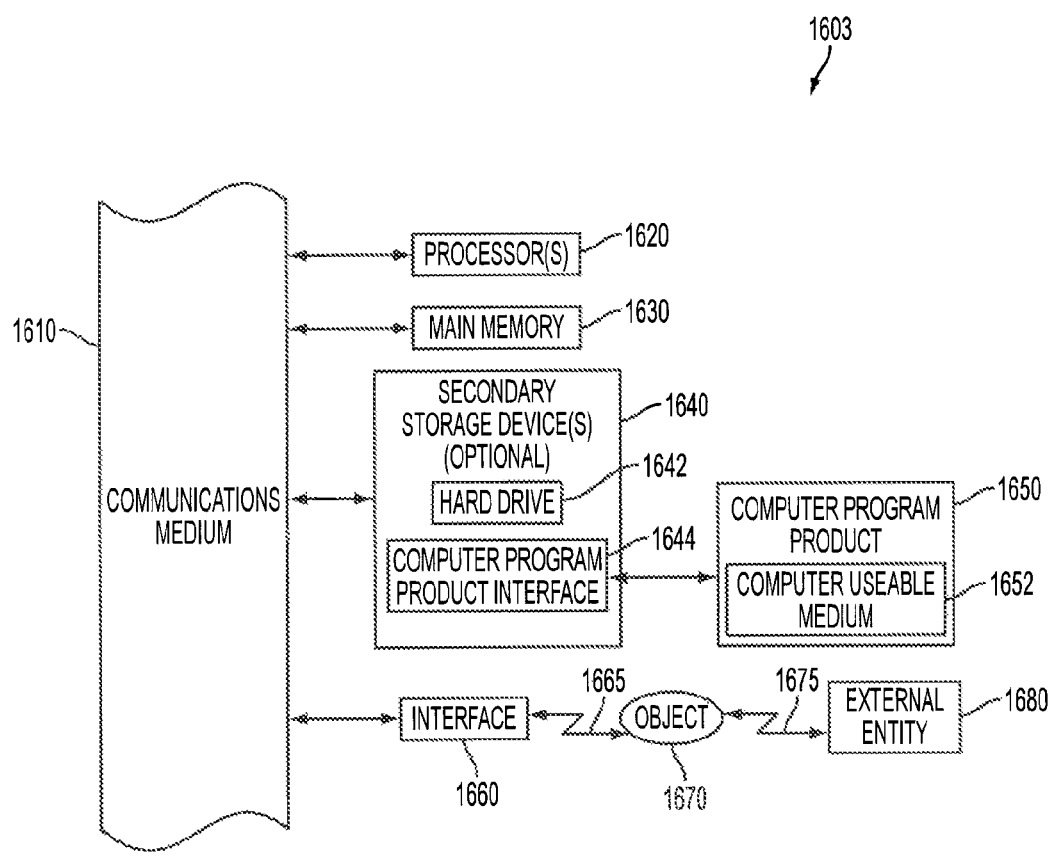
FIG. 16 illustrates a block diagram of a data processing unit that can be used to implement portions of the RFID reader/sensor or controller illustrated in FIG. 12.

FIG. 16 illustrates a block diagram of a data processing unit 1603 that can be used to implement portions of the RFID reader/sensor or controller illustrated in FIG. 12. It is noted that the entities shown in FIG. 12 may be implemented using any number of data processing units 1603, and the configuration actually used is implementation specific.

Data processing unit 1603 may represent a computer, a hand-held computer, a lap top computer, a personal digital assistant, a mobile phone, and/or any other type of data processing device. The type of data processing device used to implement the entities shown in FIG. 12 is implementation specific.

Data processing unit 1603 includes a communications medium 1610 (such as a bus, for example) to which other modules are attached.

Data processing unit 1603 also includes one or more processors 1620 and a main memory 1630. Main memory 1630 may be RAM, ROM, or any other memory type, or combinations thereof.

Data processing unit 1603 may also include secondary storage devices 1640 such as but not limited to hard drives 1642 or computer program product interfaces 1644. Computer program product interfaces 1644 are devices that access objects (such as information and/or software) stored in computer program products 1650. Examples of computer program product interfaces 1644 include, but are not limited to, floppy drives, CD drives, DVD drives, ZIP drives, JAZ drives, optical storage devices, universal serial bus (USB), etc. Examples of computer program products 1650 include, but are not limited to, floppy disks, CDs, DVDs, ZIP and JAZ disks, memory sticks, memory cards, or any other medium on which objects may be stored.

The computer program products 1650 include a computer useable medium 1652 on which objects may be stored, such as but not limited to optical mediums, magnetic mediums, etc.

Control logic or software may be stored in main memory 1630, second storage device(s) 1640, and/or computer program products 1650.

More generally, the term "computer program product" refers to any device in which control logic (software) is stored, so in this context a computer program product could be any memory device having control logic stored therein. The invention is directed to computer program products having stored therein software that enables a computer/processor to perform functions of the invention as described herein.

The data processing unit 1603 may also include an interface 1660 which may receive objects (such as data, applications, software, images, etc.) from external entities 1680 via any communications media including wired and wireless communications media. In such cases, objects 1670 are transported between external entities 1680 and interface 1660 via signals 1665, 1675. In other words, signals 1665, 1675 include or represent control logic for enabling a processor or computer to perform the functions of the invention. According to embodiments of the invention, such signals 1665, 1675 are also considered to be computer program products, and the invention is directed to such computer program products.

CONCLUSION

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method for monitoring pressure at one or more points on an individual and automatically adjusting one or more sections of a support structure having a plurality of adjustable cells, wherein the support structure is divided into a plurality of zones and one or more of the zones is divided into a plurality of subzone, the method comprising:
    periodically receiving with one or more processors, localized contact pressure data from one or more radio frequency (RF) addressable sensors placed on an individual;
    determining whether an adjustment in the support structure is required using the received localized contact pressure data
    when an adjustment is required, systematically adjusting cells located within the plurality of zones, one zone at a time, until a required change in localized pressure data is indicated;
    if the required change in localized pressure data is indicated for a zone, systematically adjusting cells within, the plurality of subzones for that zone, one subzone at a time, until the required change in localized pressure data is indicated; and
    if the required change in localized pressure data is indicated for a subzone, systematically adjusting cells in that subzone, one cell at a time, until the required change in localized pressure data is indicated.

2. The method of claim 1, further comprising receiving a tag identification number for each of the one or more RI' addressable sensors.

3. The method of claim 1, wherein receiving localized contact pressure data from one or more RF addressable sensors includes polling the RF addressable sensors.

4. The method of claim 1, wherein determining whether an adjustment is required includes determining whether the received localized contact pressure data from one or more of the RF addressable sensors exceeds a threshold.

5. The method of claim 1, wherein determining whether an adjustment is required is based on a historical trend for one or more of the RF addressable sensors.

6. The method of claim 5, wherein the historical trend includes information indicating that the received localized contact pressure data has increased over a predetermined period of time.

7. The method of claim 1, wherein an order for systematically adjusting one or more zones is based on the likely position of the individual on the support structure.

8. The method of claim 1, wherein an order for systematically adjusting one or more zones is based on the likelihood or severity of a pressure injury occurring in the zone.

9. The method of claim 1, wherein determining whether an adjustment in the support stricture is required is based on whether the received localized contact pressure data is below a threshold pressure.

10. The method of claim 1, further comprising
    sending an alert to an external monitoring station if the required change in the pressure data is not indicated after the adjustments are completed.

11. The method of claim 1, further comprising:
    maintaining the adjustments for a predetermined period of time; and
    receiving updated localized contact pressure data from the one or more RF addressable sensors.

12. The method of claim 11, further comprising:
    returning one or more of the adjustable sections to a pre-adjusted level following the predetermined period of time.

13. The method of claim 1, wherein adjusting one or more identified sections includes inflating one or more of the identified sections.

14. The method of claim 1, wherein adjusting one or more identified sections includes deflating one or more of the identified sections.

15. A system for preventing and/or treating pressure wounds on an individual, the system comprising:
    a support structure including a plurality of adjustable cells, wherein the support structure is divided into a plurality of zones and one or more of the zones is divided into a plurality of subzones;
    an RFID sensor reader configured to receive localized contact pressure data from one or more RF addressable sensors placed adjacent to the skin of the individual;
    a processor coupled to the support structure and the RE sensor reader, wherein the processor is configured to:
    determine whether the localized contact pressure data in an RF addressable sensor in the one or more RF addressable sensors exceeds a predetermined threshold, and
    isolate a location on the individual of the RF addressable sensor by systematically adjusting the adjustable cells in the plurality of zones, one zone at a time until a required change in the localized contact pressure data is indicated for a zone and adjusting the adjustable cells in the plurality of subzones for that zone, one subzone at a time, until the required change in the localized contact pressure data is indicated.

16. The system of claim 15, further comprising an actuator coupled to the processor and the one or more adjustable cells.

17. The system of claim 16, further comprising a hose assembly connected to the one or more adjustable sections, the hose assembly comprising:
   a means of introducing pressure;
   a central line operatively connected to the means of introducing pressure; and
   one or more branch lines operatively connected to the central line and operatively connected to the one or more adjustable sections,
   wherein the hose assembly is configured to adjust the one or more identified sections.

18. The system of claim 17, wherein the hose assembly is configured to adjust the one or more identified sections with air pressure.

19. The system of claim 17, wherein the hose assembly is configured to adjust the one or more identified sections with fluid pressure.

20. The system of claim 15, wherein the RF addressable sensor is included in a bandage affixed to the skin of the individual.

21. The system of claim 15, wherein the support structure is a bed.

22. The system of claim 15, wherein the support structure is a pad configured for use on a bed.

23. The system of claim 15, wherein the support structure is a chair.

24. The system of claim 15, wherein the support structure is a wheel chair.

25. The system of claim 15, wherein the support structure is a pad configured for use on a chair.

* * * * *